United States Patent
Kroll et al.

(10) Patent No.: US 6,445,950 B1
(45) Date of Patent: Sep. 3, 2002

(54) IMPLANTABLE CARDIOVERTER/ DEFIBRILLATOR EMPLOYING SHOCK DELIVERY TIMING FOR PREVENTING INDUCED FIBRILLATION

(75) Inventors: Mark W. Kroll, Simi Valley; Steven W. Badelt, Granada Hills; Gabriel A. Mouchawar, Newhall, all of CA (US)

(73) Assignee: Pacesetter, Sylmar, CA (US)

( * ) Notice: Subject to any disclaimer, the term of this patent is extended or adjusted under 35 U.S.C. 154(b) by 0 days.

(21) Appl. No.: 09/630,238

(22) Filed: Aug. 1, 2000

(51) Int. Cl.$^7$ ................................................ A61N 1/39
(52) U.S. Cl. .................................................... 607/4
(58) Field of Search .............................. 607/4, 5, 9, 11, 607/14

(56) References Cited

U.S. PATENT DOCUMENTS 5,007,422 A * 4/1991 Pless et al. .................. 607/4
5,074,301 A * 12/1991 Gill ............................ 607/4
6,256,534 B1 * 7/2001 Dahl ........................... 607/5

* cited by examiner

*Primary Examiner*—Kennedy Schaetzle
*Assistant Examiner*—Kristen Droesch

(57) ABSTRACT

An implantable cardioverter/defibrillator applies a quantity of electrical energy to a heart to terminate an arrhythmia of the heart. The cardioverter/defibrillator employs therapy delivery timing to avoid delivery of the therapy during vulnerable periods of the heart. The cardioverter/ defibrillator includes an arrhythmia detector that detects an arrhythmia of the heart, a ventricular activation detector that detects ventricular activations of the heart, and an atrial activation detector that detects atrial activations of the heart. A ventricular timer, resettable by detected ventricular activations, and an atrial timer, resettable by detected atrial activations, keep time responsive to the arrhythmia detector detecting the arrhythmia. A generator applies the quantity of electrical energy to the heart responsive to the arrhythmia detector detecting the arrhythmia, when neither chamber is in its vulnerable period.

9 Claims, 4 Drawing Sheets

IMPLANTABLE CARDIOVERTER/DEFIBRILLATOR EMPLOYING SHOCK DELIVERY TIMING FOR PREVENTING INDUCED FIBRILLATION

FIELD OF THE INVENTION

The present invention generally relates to an implantable cardioverter/defibrillator. The present invention more particularly relates to such a cardioverter/defibrillator having arrhythmia termination shock delivery timing which avoids shock delivery during vulnerable periods of the heart.

BACKGROUND OF THE INVENTION

There is an increasing problem with ventricular defibrillation and cardioversion shocks causing atrial fibrillation. This is due to the tendency towards the use of a "single-pass" lead, the use of a "hot can" and the progressive decreasing of energy requirements for ventricular cardioversion and defibrillation. The single-pass lead, of the type known in the art, includes an atrial or superior vena cava shock coil for positioning in the right atrium or superior vena cava and a ventricular shock coil for positioning in the right ventricle. Hot can usage encompasses the use of the electrically conductive device enclosure as a defibrillation electrode wherein the cardioversion or defibrillation shocks are delivered from the ventricular shock coil to the atrial/superior vena cava shock coil and the electrically conductive device enclosure. Prior to the hot can approach, a subcutaneous patch electrode was used. The hot can approach causes more current flow through the atria than was caused when using the subcutaneous patch.

Extremely high energy shocks cardiovert or defibrillate the entire heart and thus preclude induction of atrial fibrillation during ventricular cardioversion or defibrillation. However, the trend is to employ more moderate energy shocks for ventricular cardioversion and defibrillation. These reduced energy shocks may not cardiovert or defibrillate the atria during ventricular cardioversion and defibrillation thus increasing the probability of inducing atrial fibrillation as a result of ventricular cardioversion or defibrillation.

The induction of atrial fibrillation by ventricular arrhythmia shock therapy causes a cascading sequence of problems. The delivery of the ventricular shock usually occurs during a period of patient unconsciousness and is not felt. However, after atrial fibrillation is induced, the patient is left with significant anxiety that there is still an arrhythmia. This can lead to inappropriate decisions on the part of the patient, as well as the implantable ventricular cardioverter/defibrillator. For example, the implanted device can mistake the atrial fibrillation for a ventricular arrhythmia and thus cause another shock to be delivered to the patient. This second shock is often extremely painful, for the patient will now be conscious. The second delivered shock, moreover, will most likely merely serve to ensure that the patient remains in atrial fibrillation.

The atrial period of vulnerability is a period of time during which atrial fibrillation is more easily induced and is analogous to the ventricular period of vulnerability. It follows shortly after the P-wave. Ventricular shocks delivered during this period are more likely to induce atrial fibrillation.

Generally, ventricular defibrillation shocks are delivered synchronized to a sensed R-wave to avoid the potential ventricular fibrillation induction in the case of a false positive ventricular fibrillation discrimination. Therefore, in a ventricular defibrillator also employing dual chamber pacing, ventricular defibrillation shock timing would be advantageous. It would also be advantageous to base shock timing on both the atrial and ventricular intrinsic and paced activity. The same reasoning applies equally as well to an atrial defibrillation shock and the induction of ventricular fibrillation.

SUMMARY OF THE INVENTION

The invention provides an implantable cardioverter/defibrillator which applies a quantity of electrical energy to a heart to terminate an arrhythmia of the heart. The cardioverter/defibrillator employs therapy delivery timing to avoid delivery of the therapy during vulnerable periods of the heart. The cardioverter/defibrillator includes an arrhythmia detector that detects a ventricular or atrial arrhythmia of the heart, a ventricular activation detector that detects ventricular activations of the heart, and an atrial activation detector that detects atrial activations of the heart. A ventricular timer, resettable by detected ventricular activations, and an atrial timer, resettable by detected atrial activations, keep time responsive to the arrhythmia detector detecting the arrhythmia. A generator applies the quantity of electrical energy to the heart responsive to the arrhythmia detector detecting the arrhythmia, the ventricular timer, and the atrial timer.

In accordance with a primary aspect of the present invention, the ventricular timer and atrial timer of the implantable cardioverter/defibrillator keep time through vulnerable intervals corresponding to vulnerable periods of the ventricles and atria respectively and the generator withholds application of the quantity of electrical energy to the heart responsive to one of the timing means being in a vulnerable interval.

In accordance with another aspect of the present invention the ventricular timer and atrial timer of the implantable cardioverter/defibrillator keep time through safe intervals corresponding to absolute refractory and rest periods of the ventricles and atria respectively and the generator applies the quantity of electrical energy to the heart responsive to both of the timers being in one of the safe intervals.

The invention further provides an implantable cardioverter/defibrillator which applies a quantity of electrical energy to a heart to terminate a ventricular arrhythmia. The cardioverter/defibrillator includes a ventricular arrhythmia detector that detects ventricular arrhythmias, an atrial activation detector that detects atrial activations, and a generator that delivers the quantity of electrical energy to the heart responsive to the ventricular arrhythmia detector detecting a ventricular arrhythmia and at a predetermined safe time after detection of an atrial activation by the atrial activation detector.

The present invention still further provides a method of applying a quantity of electrical energy to a heart to terminate an arrhythmia of the heart. The method includes the steps of detecting a ventricular or atrial arrhythmia of the heart, detecting ventricular activations of the heart, and detecting atrial activations of the heart. The method further includes the steps of keeping a first time from each detected ventricular activation after the detection of the arrhythmia of the heart, keeping a second time from each detected atrial activation after the detection of the arrhythmia of the heart, and applying the quantity of electrical energy to the heart after detecting the arrhythmia of the heart and responsive to the first kept time and the second kept time.

In accordance with a further aspect of the present invention, the first kept time and the second kept time extend through vulnerable intervals corresponding to vulnerable periods of the ventricles and atria respectively, and application of the quantity of electrical energy to the heart is withheld when one of the kept times is in a vulnerable interval.

In accordance with further aspects of the present invention, the first kept time and the second kept time extend through safe intervals corresponding to absolute refractory and rest periods of the ventricles and atria respectively and the quantity of electrical energy is applied to the heart when both of the kept times are in one of the safe intervals.

The invention still further provides a method of applying a quantity of electrical energy to a heart to terminate a ventricular arrhythmia including the steps of detecting a ventricular arrhythmia of the heart, detecting atrial activations of the heart, and delivering the quantity of electrical energy to the heart after detecting the ventricular arrhythmia and a predetermined time after detecting an atrial activation.

BRIEF DESCRIPTION OF THE DRAWINGS

The features of the present invention which are believed to be novel are set forth with particularity in the appended claims. The invention, together with further objects and advantages thereof may best be understood by making reference to the following description taken in conjunction with the accompanying drawings, in the several figures of which like reference numerals identify identical elements, and wherein:

DETAILED DESCRIPTION OF THE PREFERRED EMBODIMENTS

Figure 1:
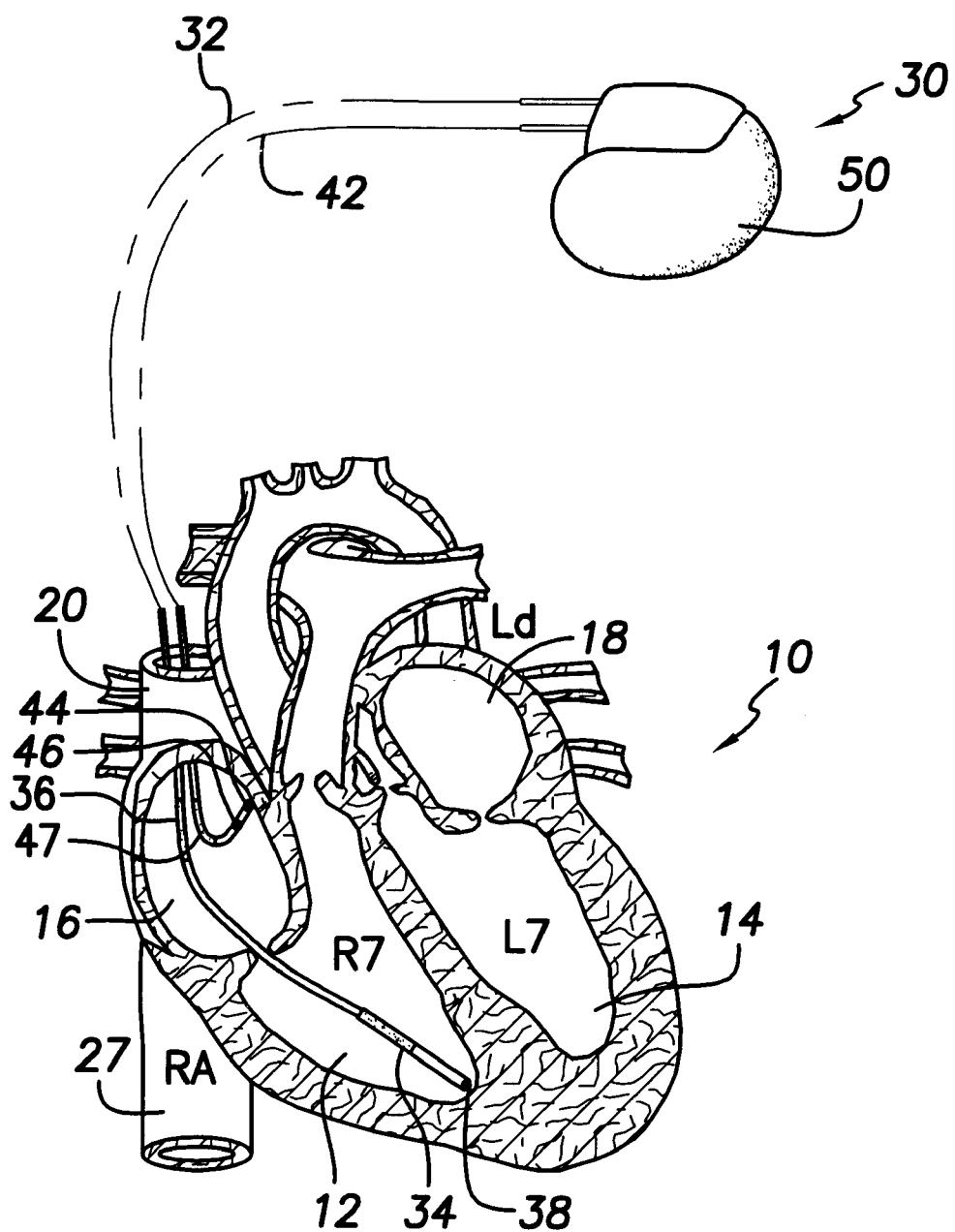
FIG. 1 is a schematic illustration of a human heart in need of ventricular arrhythmia cardioversion/defibrillation shown in association with an implantable ventricular cardioverter/defibrillator embodying the present invention.

Referring now to FIG. 1, it illustrates a heart 10 in need of ventricular and/or atrial arrhythmia cardioversion/ defibrillation and an associated implantable ventricular and atrial cardioverter/defibrillator 30 embodying the present invention. The portions of the heart 10 illustrated in FIG. 1 are the right ventricle 12, the left ventricle 14, the right atrium 16 and the left atrium 18. Also illustrated are the superior vena cava 20 and inferior vena cava 27. As is well known in the art, the cardioverter/defibrillator 30 is arranged to be implanted in an upper left chest portion of a patient within a subcutaneous pocket.

The implantable device 30 includes a first endocardial lead 32, which is of the "single-pass" type. To that end, the lead 32 includes a first shock coil 34 arranged to be disposed within the right ventricle 12 and a second shock coil 36 proximal to the shock coil 34 and arranged to be disposed within the superior vena cava 20 and/or the right atrium 16. The lead 32 further includes a distal tip pacing electrode 38. The implantable device 30 further includes a second endocardial lead 42 having an electrode pair including electrode 44 and electrode 46, and shock coil 47 arranged to be disposed in the right atrium.

The implantable device 30 includes a hermetically sealed, electrically conductive enclosure 50. When a quantity of cardioverting or defibrillating electrical energy is applied to the ventricles of the heart 10, in accordance with this preferred embodiment, electrode 36 and the enclosure 50 are connected in parallel and the quantity of electrical energy is applied between the parallel connected electrode 36 and enclosure 50 and the electrode 34. Alternatively, the cardioverting and defibrillating quantity of electrical energy may be applied between electrode 34 and the electrically conductive enclosure 50 without employing electrode 36. When cardioverting or defibrillating energy is applied to the atria of the heart 10, the energy may be applied between the atrial shock electrode 97 and the enclosure 50. Other cardioverting or defibrillating electrode configurations are known in the art and may be employed without departing from the present invention.

Figure 2:
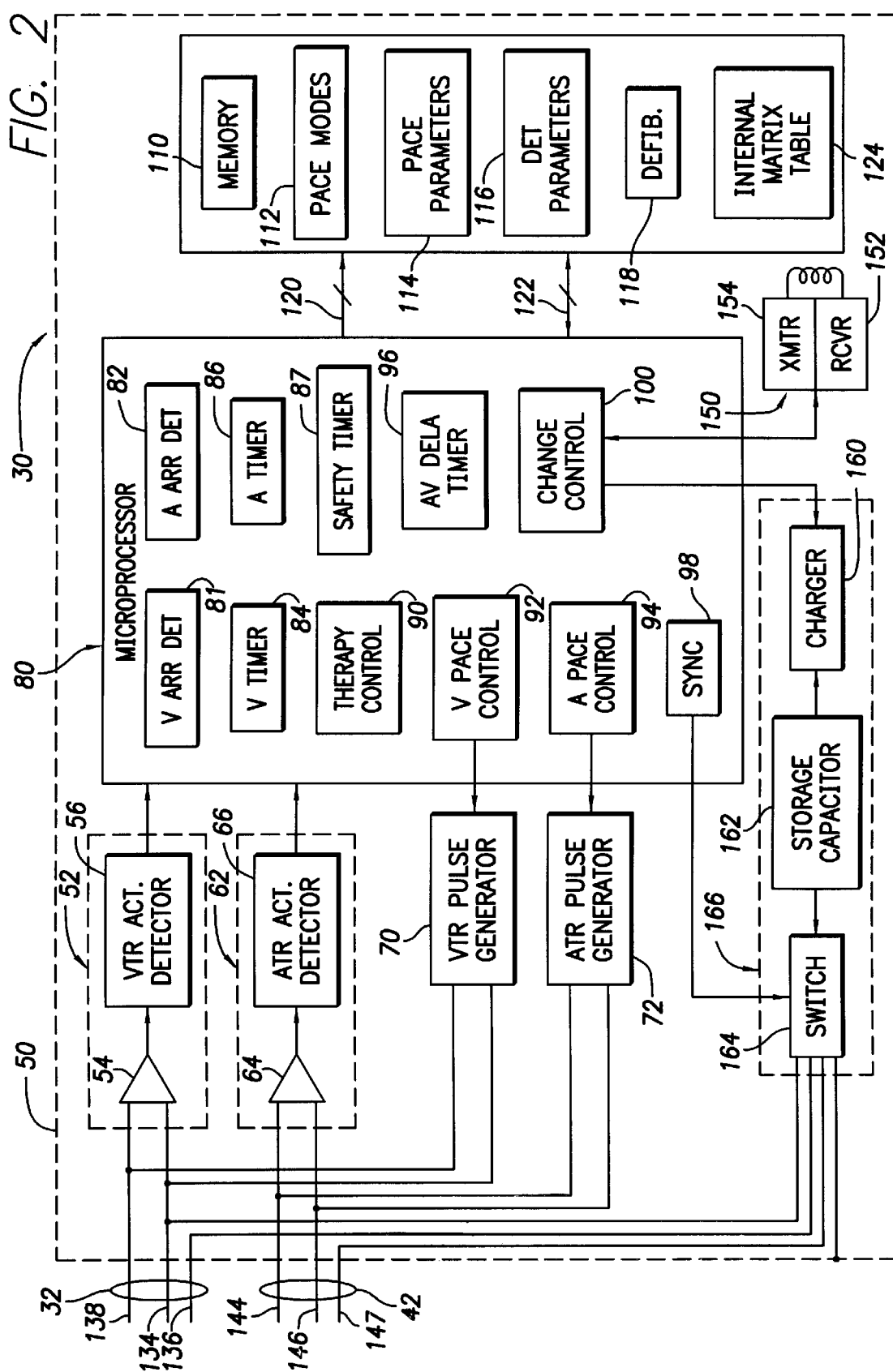
FIG. 2; is a block diagram of the implantable ventricular cardioverter/defibrillator of FIG. 1.

As illustrated in FIG. 2, the implantable device 30 includes within the enclosure 50 a ventricular sense channel 52, an atrial sense channel 62, and a pacing pulse generator 70 including a first or atrial pulse generator 72 for providing atrial pacing pulses and a second or ventricular pulse generator 74 for providing ventricular pacing pulses. The device 30 further includes a microprocessor 80, a memory 110, a telemetry stage 150, and a generator 166 for applying the quantity of electrical energy to the heart 10 to terminate an arrhythmia of the heart.

The ventricular sense channel 52 includes a sense amplifier 54 and an activation detector 56, or event detector, such as a threshold detector that detects ventricular electrical activity, including intrinsic R-waves and fibrillation signals (hereinafter referred to as ventricular activations). The sense amplifier 54 has an input coupled to the distal electrode 38 of lead 32 by a conductor 138 of lead 32. The sense amplifier 54 has another input, which is coupled to electrode 34 of lead 32 by a conductor 134 of lead 32. The sense amplifier 54 further has an output which forms an input to the activation detector 56. As further illustrated, the activation detector 56 has an output, which is coupled to the microprocessor 80.

The sense amplifier 54, together with electrodes 38 and 34, senses electrical activity in the right ventricle 12. In accordance with this embodiment, when the output from the amplifier 54 transitions through a programmed threshold of the activation detector 56, the activation detector 56 provides an input signal to the microprocessor 80 indicating that a ventricular activation has been detected. Such ventricular activation detection is well known in the art. Other detection methods, such as slope detection or morphology comparison, may be employed without departing from the present invention.

Similarly, the atrial sense channel 62 includes a sense amplifier 64 and an atrial activation detector 66, or event detector, such as a threshold detector. The sense amplifier 64 has an input, which is coupled to electrode 44 of lead 42 by a conductor 144 of lead 42. The sense amplifier 64 has another input, which is coupled to electrode 46 of lead 42 by another conduct 146 of lead 42. The sense amplifier 64 has an output, which forms an input to the activation detector 66. As further illustrated, the activation detector 66 has an output, which is coupled to the microprocessor 80.

The sense amplifier 64, together with electrodes 44 and 46, senses electrical activity or activation in the right atrium, including intrinsic P-waves and fibrillation signals (sometimes referred to as AF-wave, F-waves, or Fib-waves). When the output of the sense amplifier 64 transitions through a programmed threshold of the activation detector 66, the activation detector 66 provides an input signal to the microprocessor 80 indicating that an atrial activation or P-wave has been detected. Such detection is also well known in the art. Again, other atrial activation detection methods may be employed without departing from the present invention.

The first or atrial pulse generator 72 has outputs coupled to electrodes 44 and 46 through conductors 144 and 146 respectively of lead 42. This permits pacing pulses produced by the first generator 72 to be applied to the right atrium 16. The second or ventricular pacing pulse generator 74 has outputs coupled to electrodes 38 and 34 by conductors 138 and 134 respectively of lead 32. This permits pacing pulses produced by the second generator 74 to be applied to the right ventricle 12. Other ventricular pacing electrode configurations, such as a dedicated bipolar electrode pair, may be employed.

The overall functioning of the device 30 is controlled by the microprocessor 80. The microprocessor 80 implements selected pacing and arrhythmia termination modalities by executing operating instructions stored in the memory 110. The pacing mode operating instructions are stored in a memory portion 112 and the arrhythmia termination operating instructions are stored in a memory portion 118. In executing the pacing operating instructions, the microprocessor 80 further utilizes pacing parameters stored in memory portion 114 and detection parameters stored in memory portion 116. The pacing parameters may include AV delays, atrial and ventricular pacing energies, atrial and ventricular escape intervals, and basic rates for example. The detection parameters may include blanking period durations, refractory periods, and detection thresholds for the threshold detectors 56 and 66, for example. Such pacing parameters and detection parameters are well known in the art.

In executing the arrhythmia termination operating instructions, the microprocessor 80, in accordance with the present invention, utilizes an interval matrix table stored in memory portion 124. As will be seen hereinafter, the interval matrix table is accessed by the microprocessor 80 to determine whether to apply cardioverting or defibrillating electrical energy to the heart. The memory portion 124 may further include subroutines associated with the application of the arrhythmia terminating electrical energy.

The telemetry stage 150 permits mode selections and storage of pacing and arrhythmia termination parameters in memory 110 to be made through the use of an external programmer (not shown) of the type well known in the art. The telemetry stage includes a receiver 152, which receives telemetry commands including mode selection commands and pacing and arrhythmia termination parameters from the programmer. The receiver 152 conveys the commands to the microprocessor 80, which then stores hem in the memory 110.

The telemetry stage 150 also includes a transmitter 154. The transmitter may be used for transmitting data to the programmer. The transmitted data may include sensed electrograms or status information, for example, as is well known in the art.

The microprocessor 80 is coupled to the memory 110 by a multiple-bit address bus 120 and a bidirectional, multiple-bit data bus 122. The microprocessor 80 uses the address bus 120 to fetch operating instructions or programmable parameters from the memory at address locations defined on the address bus 120. The fetched instructions and parameters are conveyed to the microprocessor 80 over the data bus 122. Similarly, the microprocessor 80 may store data in the memory 110 at memory locations defined on the address bus 120. The microprocessor 80 conveys the data to the memory over the data bus 122. Such microprocessor and memory operation is conventional in the art.

The generator 166 includes a charger 160, a storage capacitor 162, and a switch 164. When an arrhythmia of the heart is detected, the charger 160 is commanded by the microprocessor to charge the storage capacitor 162 to an appropriate voltage or energy level depending upon the type of arrhythmia to be terminated. When the storage capacitor 162 is charged to the appropriate level, the switch 164 is then operated by the microprocessor 80 to apply the cardioverting or defibrillating electrical energy to the corresponding appropriate electrode configuration. To that end, the switch includes a first output, which is coupled to shock coil 34 of lead 32 by the conductor 134 of lead 32. The switch 164 also includes another output, which is coupled to the shock coil 36 of lead 32 by another conductor 136 of lead 32. The switch 164 still further includes an output, which is coupled to the atrial shock coil electrode 47 of lead 42 by another conductor 147 of lead 42. Lastly, the switch 164 is coupled to the electrically conductive enclosure 50 of the implantable device 30. As a result, when ventricular fibrillation is to be terminated, the switch 164 is operated to apply the defibrillating electrical energy between the shock coil 34 and the parallel connected enclosure 50 and shock coil electrode 36. When atrial fibrillation is to be terminated, the switch 164 is operated to apply the defibrillating energy between shock coil electrode 47 and the enclosure 50.

When executing the operating instructions stored in memory 110, the microprocessor 80 implements a number of functional stages. Those stages include a ventricular arrhythmia detector 81, an atrial arrhythmia detector 82, a first or ventricular timer 84, a second or atrial timer 86 and a safety timer 87. The functional stages further include a therapy control 90 which includes a ventricular pacing control 92, an atrial pacing control 94, an AV delay timer 96, a synchronization stage 98, and a charge control 100.

In accordance with a first aspect of the present invention, a ventricular arrhythmia terminating shock is applied to the heart 10 in such a way as to avoid the vulnerable period of the atria. To that end, when the ventricular arrhythmia detector 82 detects a ventricular arrhythmia, the capacitor 162 is immediately charged by the charger 160 to a given programmable energy level. The charge control 100 determines when the capacitor has been charged to the given level. Before the capacitor has been charged to the given level, for example upon detection of the arrhythmia or when charging begins, the atrial timer 86 is started and keeps time. The timer 86 is reset by the first detected atrial activation. After the capacitor is charged and when the timer 86 times a predetermined time interval which is safely past the atrial vulnerable period, the therapy control 90 causes the switch 164 to operate to apply the ventricular arrhythmia terminating quantity of electrical energy to the heart through the switch 164. The predetermined time safely past the atrial vulnerable period may be on the order of about 300 milliseconds.

Alternatively, the timer 86 may be started by the charge control 100 upon the detection of the first atrial activation following the charging of capacitor 162 to the given level. Further, in accordance with the present invention, the arrhythmia terminating electrical energy may be applied directly after the first atrial activation is detected following the charging of the capacitor 162 to the given level. This will apply the electrical energy to the heart before the atrial period of vulnerability. For example, in accordance with this aspect of the present invention, the electrical energy may be applied within about 30 milliseconds after the detection of the atrial activation.

As an alternative embodiment, the electrical energy may be applied substantially synchronized to an atrial pacing pulse. In accordance with this embodiment, if an atrial activation is not detected within a given escape interval, the therapy control 90 may cause the atrial pace control 94 to cause the atrial pacer 72 to apply an atrial pacing pulse to the right atrium. Immediately following the atrial pacing pulse, and thus substantially synchronized to the atrial pacing pulse, the therapy control 90 operates switch 164 to apply the arrhythmia terminating electrical energy to the heart.

In accordance with a further aspect of the present invention, the delivery of the arrhythmia terminating electrical energy may be based on timing of both of the atrium and ventricle of the heart. To that end, both the first or ventricular timer 84 and the second or atrial timer 86 may be utilized for keeping time following the detection of either an atrial or ventricular arrhythmia of the heart. As will be noted in FIG. 3, the ventricular timer, which is resettable by detected ventricular activations and applied pacing pulses, keeps time through three timer intervals 202, 204, and 206 of the ventricular electrogram 200. The interval 202 is a ventricular absolute refractory interval corresponding to the ventricular absolute refractory period of the ventricles. Interval 204 is a ventricular vulnerable interval corresponding to the ventricular period of vulnerability. Interval 206 is a ventricular rest interval corresponding to the ventricular rest period of the ventricles.

The intervals are cyclically congruent to one another such that the end of the ventricular absolute refractory interval is equal to the start of the ventricular vulnerability interval, the end of the ventricular vulnerability interval is equal to the start of the ventricular rest interval, and the end of the ventricular rest interval is equal to the start of the ventricular absolute refractory interval. Interval 202 may extend from 0 to 30 milliseconds, interval 204 may extend from 31 milliseconds to 300 milliseconds, and interval 206 may extend from 301 milliseconds to 500 milliseconds, for example. As will be appreciated by those skilled in the art, the interval durations may be programmable parameters. Further, because the interval durations may vary widely from patient to patient, they may be tailored to an individual patient. Hence, the intervals stated above are provided as being exemplary only. Insofar as the ventricles are concerned, the ventricular absolute refractory interval 202 and the ventricular rest interval 206 are safe intervals in which to deliver the arrhythmia terminating electrical energy. In contrast, the ventricular vulnerability interval 204 is an unsafe interval in which to deliver the arrhythmia terminating electrical energy.

Similarly, the second or atrial timer 86 is resettable by detected atrial activations and applied atrial pacing pulses. The atrial timer also keeps time through three timed intervals 212, 214, and 216 of the atrial electrogram 210. Interval 212 is an atrial absolute refractory interval corresponding to the atrial absolute refractory period of the atria. Interval 214 is an atrial vulnerable interval corresponding to the atrial period of vulnerability. Interval 216 is an atrial rest interval corresponding to the atrial rest period of the atria.

Again, the intervals are cyclically congruent to one another such that the end of the atrial absolute refractory interval is equal to the beginning of the atrial vulnerable interval, the end of the atrial vulnerable interval is equal to the start of the atrial rest interval, and the end of the atrial rest interval is equal to the start of the atrial absolute refractory interval. Interval 212 may extend from 0 milliseconds to 30 milliseconds, interval 214 may extend from 31 milliseconds to 300 milliseconds, and interval 206 may extend from 301 milliseconds to 500 milliseconds, for example. Again, for the same reasons expressed previously, the above-stated intervals are provided as being exemplary only. Insofar as the atria are concerned, the atrial absolute refractory interval 212 and the atrial rest interval 216 are safe intervals in which to deliver the arrhythmia terminating electrical energy to the heart while the atrial vulnerable interval 214 is an unsafe interval in which to deliver the arrhythmia terminating electrical energy.

Figure 3:
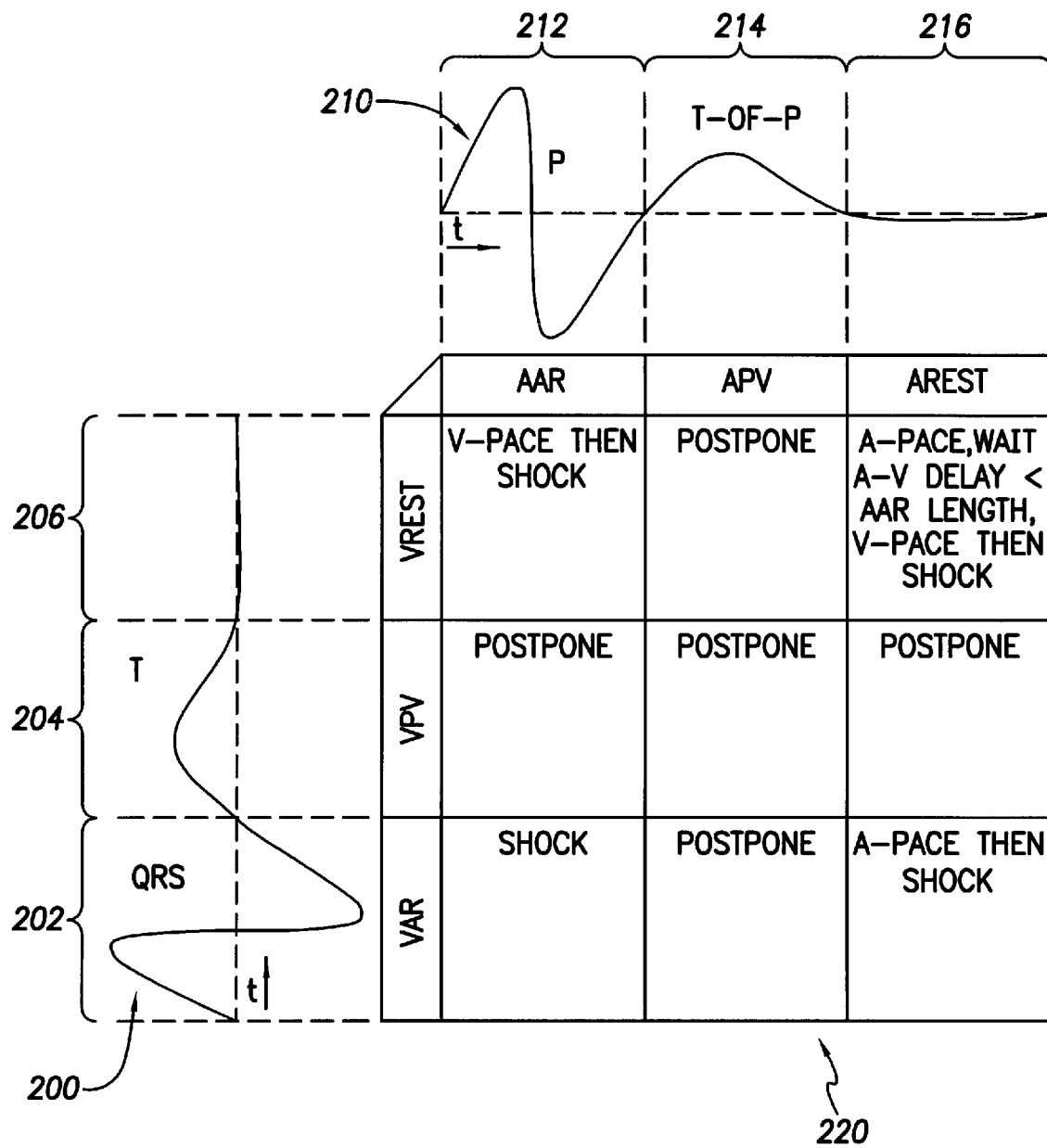
FIG. 3 shows illustrative ventricular and atrial electrograms disposed to demonstrate respective absolute refractory, vulnerable, and rest intervals and a matrix of preferred therapies for the interval combinations in accordance with the present invention.

As can thus be noted in FIG. 3, a 3×3 table or matrix 220 may be stored in memory portion 124 of memory 110 to indicate in which of nine possible states the heart is in at any one time. The table indicates the action to be taken for each state regardless of whether a ventricular arrhythmia or atrial arrhythmia is to be terminated. The entry state is that state during which the charging of capacitor 162 to the given energy level is completed. The exit state is the command to deliver the arrhythmia terminating electrical energy to the heart.

In summary, the ventricular timer 84 and atrial timer 86 are adapted to keep time through vulnerable intervals corresponding to vulnerable periods of the ventricles and atria respectively and safe intervals corresponding to absolute refractory and rest periods of the ventricles and atria respectively. When the capacitor 162 is fully charged, the delivery of the arrhythmia terminating electrical energy will be withheld if one of the timers is in a vulnerable interval and will be delivered when both of the timers are in one of the safe intervals. If at the time the capacitor 162 is fully charged, both of the timers are in one of the safe intervals, the arrhythmia terminating electrical energy will be immediately applied to the heart.

As will be noted in the matrix 220 of FIG. 3, if at the time the capacitor 162 is fully charged the ventricular timer is in the ventricular rest interval 206 while the atrial timer is in the atrial absolute refractory interval 212, the right ventricle may first be paced prior to delivery of the arrhythmia terminating electrical energy. Here, the ventricular pace control 92 causes the ventricular pacer 74 to deliver a pacing pulse to the right ventricle. Substantially synchronized with that pacing pulse, the synchronizing stage 98 will operate the switch 164 for applying the arrhythmia terminating electrical energy to the heart.

Similarly, if the ventricular timer is in the absolute refractory interval 202 and the atrial timer is in the atrial rest interval 216, an atrial pacing pulse may be applied to the right atrium just before the arrhythmia terminating electrical energy is applied. Here, the atrial pace control 94 delivers a command to the atrial pacer 72 to deliver a pacing pulse to the right atrium. Substantially synchronized with the atrial pacing pulse, the synchronizing stage 98 causes the switch 164 to operate to apply the arrhythmia terminating electrical energy to the heart.

As will be lastly noted in FIG. 3, if both the ventricular and atrial timers are in rest intervals, both the right atrium and right ventricle may be paced to control the timing of the delivery of the arrhythmia terminating electrical energy. Here, the atrial pace control 94 causes the atrial pacer 72 to deliver an atrial pacing pulse. Following the atrial pacing pulse, the AV delay timer 96 times an AV delay. The AV delay is preferably shorter than the atrial absolute refractory interval. At the end of the AV delay the ventricular pace control 92 causes the ventricular pacer 74 to deliver a ventricular pacing pulse to the right ventricle. Substantially synchronized with the ventricular pacing pulse, the synchronizing stage 98 causes the switch 164 to operate for applying the arrhythmia terminating electrical energy to the heart.

If at the time the capacitor 162 is fully charged both the ventricular and atrial timers are in the absolute refractory intervals, the switch 164 may be immediately operated. This will cause the arrhythmia terminating electrical energy to be immediately applied to the heart.

Figure 4:
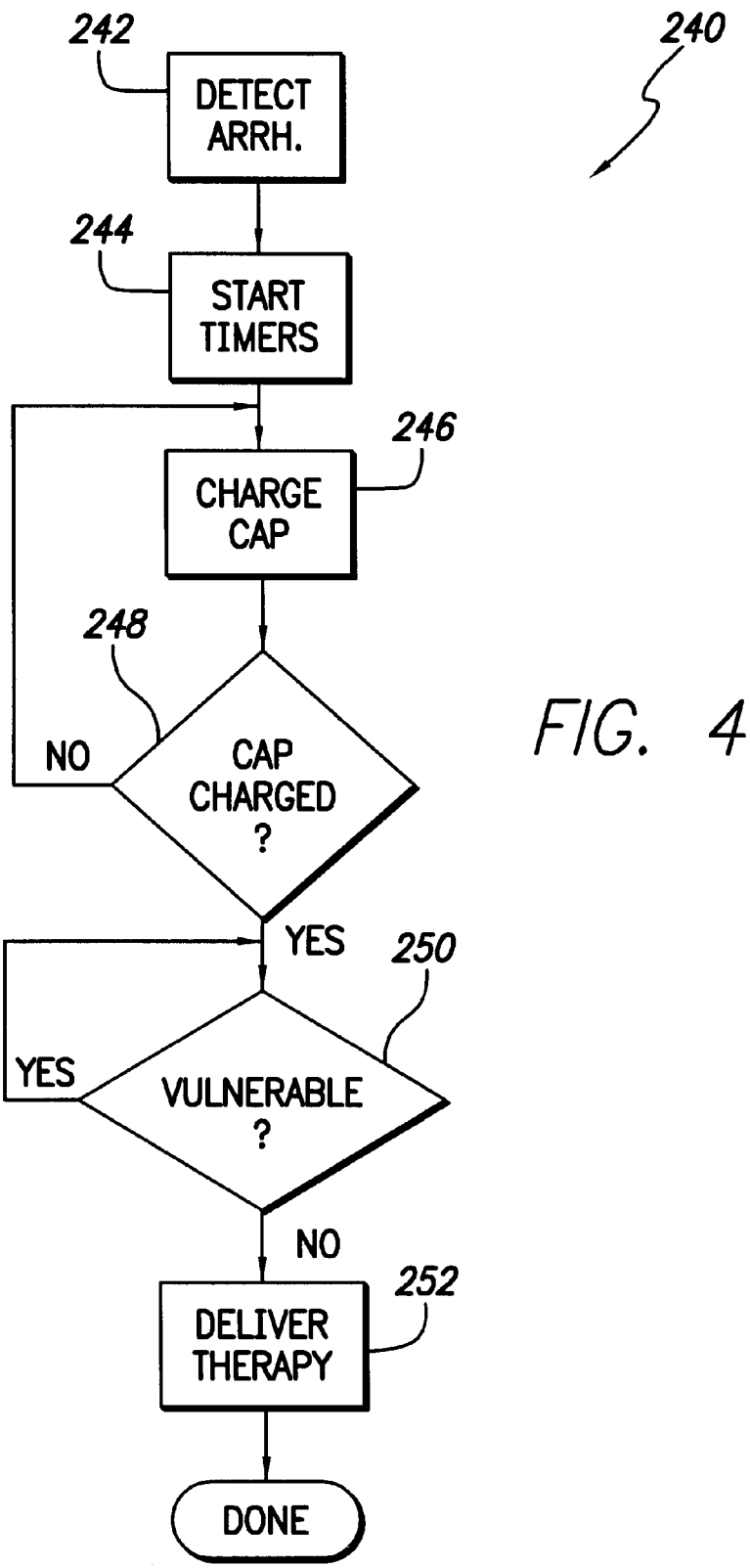
FIG. 4 is a flow diagram illustrating operative steps that the device of FIGS. 1 and 2 may implement in accordance with a preferred embodiment of the present invention.

Referring now to FIG. 4, it best summarizes the foregoing implementation of the present invention and is equally applicable to the termination of either a ventricular arrhythmia or an atrial arrhythmia. The flow diagram 240 begins at step 242 wherein either the ventricular arrhythmia detector 81 or atrial arrhythmia detector 82 detects an arrhythmia of the ventricles or atria, respectively, of the heart. In step 244 responsive to the arrhythmia detection, the timers 86 and 84 are started. Again, these timers are reset by either detected activations of the respective chambers or the delivery of pacing pulses to their respective chambers. Also immediately after the detection of the arrhythmia in step 242, the capacitor is charged in accordance with step 246. The charge control as indicated at step 248 monitors the capacitor as it is charged. When it is fully charged, the charge control causes the therapy control to determine the state of the ventricular and atrial timers and thus if either indicates that its corresponding chamber is vulnerable in accordance with step 250. If neither timer is in a vulnerable interval, the therapy control in accordance with step 252 causes therapy to be delivered. If upon the charging of capacitor 162 one of the timers is in its vulnerable interval, the therapy control will wait until both timers are in a safe interval to deliver the therapy. Once the therapy is delivered in accordance with step 252, the process is completed.

As a result, if an atrial arrhythmia is detected by the atrial arrhythmia detector 81, therapy is delivered as previously described between electrode 47 and the enclosure 50 when both the ventricles and the atria are in safe intervals. If a ventricular arrhythmia is detected by ventricular arrhythmia detector 82, therapy is delivered between electrode 34 and the parallel connected enclosure 50 and electrode 36 when both the ventricles and atria are in a safe interval. The safety timer 87 may be employed in the event that the microprocessor 80 does not find an appropriate time to deliver therapy within a time-out period timed by the safety timer. In that event, therapy may be applied at the end of the time-out period.

While particular embodiments of the present invention have been shown and described, modifications may be made. For example, as previously mentioned, the present invention pertains equally as well to the termination of atrial arrhythmias and the prevention of inducing ventricular arrhythmias in the process. It is therefore intended to cover in the appended claims all such changes and modifications which fall within the true spirit and scope of the invention.

What is claimed is:

1. An implantable cardioverter/defibrillator which applies a quantity of electrical energy to a heart to terminate a ventricular arrhythmia, the cardioverter/defibrillator comprising:

ventricular arrhythmia detecting means for detecting a ventricular arrhythmia;

atrial activation detecting means for detecting atrial activations;

timing means for defining a vulnerable period related to an atrial activation detected by the atrial activation detector; and generating means for delivering the quantity of electrical energy to the heart responsive to the ventricular arrhythmia detecting means detecting a ventricular arrhythmia and at a predetermined safe time after detection of an atrial activation by the atrial activation detecting means which avoids the vulnerable period.

2. The implantable cardioverter/defibrillator of claim 1 further including timing means responsive to the arrhythmia detecting means and the atrial activation detecting means for timing the predetermined time from a first atrial activation detected after the arrhythmia detecting means detects a ventricular arrhythmia, and wherein the generating means delivers the quantity of electrical energy responsive to the timing means timing the predetermined time.

3. The implantable cardioverter/defibrillator of claim 1 further including atrial pacing means for applying a pacing pulse to an atrium of the heart in the absence of an atrial activation being detected within a given time and wherein generating means is responsive to the atrial pacing means for delivering the quantity of electrical energy to the heart immediately after the pacing means applies the pacing pulse to the atrium.

4. An implantable cardioverter/defibrillator which applies a quantity of electrical energy to a heart to terminate a ventricular arrhythmia without inducing atrial fibrillation, the cardioverter/defibrillator comprising:

a ventricular arrhythmia detector, an atrial activation detector;

timing circuitry that defines a vulnerable period in response to an atrial activation detected by the atrial activation detector; and a generator that delivers the quantity of electrical energy to the heart responsive to the ventricular arrhythmia detector detecting a ventricular arrhythmia and at a predetermined time after detection of an atrial activation, wherein the predetermined time is selected to avoid the vulnerable period.

5. The implantable cardioverter/defibrillator of claim 1 further including a timer responsive to the arrhythmia detector and the atrial activation detector that commences timing to the predetermined time from a first atrial activation detected after the arrhythmia detector detects a ventricular arrhythmia, and wherein the generator delivers the quantity of electrical energy responsive to the timer timing the predetermined time.

6. The implantable cardioverter/defibrillator of claim 1 further including an atrial pacer that applies a pacing pulse to an atrium of the heart in the absence of atrial activation being detected within a given time and wherein the generator is adapted to deliver the quantity of electrical energy to the heart immediately after the atrial pacer applies the pacing pulse to the atrium.

7. A method of applying a quantity of electrical energy to a heart to terminate a ventricular arrhythmia, the method including the steps of:

detecting a ventricular arrhythmia of the heart;

detecting an atrial activation;

defining a vulnerable period related to the atrial activation; and delivering the quantity of electrical energy to the heart after detecting the ventricular arrhythmia and at a predetermined safe time after detecting an atrial activation which avoids the vulnerable period.

8. The method of claim 7 including the further step of timing the predetermined time from a first atrial activation detected after the detection of the ventricular arrhythmia, and wherein the delivering step includes delivering the quantity of electrical energy upon timing the predetermined time.

9. The method of claim 7 including the further steps of applying a pacing pulse to an atrium of the heart in the absence of an atrial activation being detected within a given time and wherein the delivering step includes delivering the quantity of electrical energy to the heart immediately after the atrial pacing pulse is applied to the atrium.

* * * * *